United States Patent [19]

Feitler

[11] 4,333,885
[45] Jun. 8, 1982

[54] METHOD FOR PRODUCING CARBOXYLIC ACID ANHYDRIDE

[75] Inventor: David Feitler, Whitehall, Pa.

[73] Assignee: Air Products and Chemicals, Inc., Allentown, Pa.

[21] Appl. No.: 250,473

[22] Filed: Apr. 2, 1981

[51] Int. Cl.$^3$ .................... C07C 51/56; C07C 51/54; C07C 53/12
[52] U.S. Cl. ................................................. 260/549
[58] Field of Search ........................................ 260/549

[56]  References Cited
U.S. PATENT DOCUMENTS

| | | | |
|---|---|---|---|
| 2,730,546 | 1/1956 | Reppe et al. | 260/549 |
| 4,046,807 | 9/1977 | Kuckertz | 260/549 |
| 4,234,719 | 11/1980 | Wan | 260/549 |

Primary Examiner—Natalie Trousof
Assistant Examiner—Frederick W. Pepper
Attorney, Agent, or Firm—Douglas G. Glantz; E. Eugene Innis; James C. Simmons

[57] ABSTRACT

A method is disclosed for the production of carboxylic acid anhydride in high yield by the carbonylation of a liquid reaction mixture comprising a carboxylic acid ester using synthesis gas in the presence of a noble metal catalyst and iodide promoter. The improved process is carried out in the presence of a carboxylic acid inhibitor, preferably having an acyl group corresponding to the acyl moiety of the carboxylic acid ester, in a side-reaction-inhibiting amount to the liquid reaction mixture. The formation of undesirable by-products, particularly methane, is reduced and a hydrogen enriched gas is produced.

10 Claims, No Drawings

METHOD FOR PRODUCING CARBOXYLIC ACID ANHYDRIDE

TECHNICAL FIELD

This invention relates to a method for producing carboxylic acid anhydrides by the carbonylation of carboxylic acid esters.

BACKGROUND OF PRIOR ART

Acetic anhydride is prepared in commercial quantities by the reaction of acetic acid with ketene, which itself is prepared by high temperature dehydration of acetic acid, e.g., in the presence of aluminum phosphate ($AlPO_4$) at a temperature of 700° C.

Reppe et al, U.S. Pat. No. 2,730,546, show the carbonylation of carboxylic acid esters with carbon monoxide in the presence of a cobalt halide catalyst at very high pressures to produce carboxylic acids, and their esters and anhydrides. The carbon monoxide may contain hydrogen which is disclosed to have some influence on the reaction product. In the absence of water, anhydrides are produced with excess carbon monoxide over hydrogen, e.g. no more than a 40% concentration of hydrogen. Reppe et al in Example 13 show reacting a mixture of methyl acetate, glacial acetic acid, anhydrous cobalt bromide, and an organic iodide and an organic bromide with 95% carbon monoxide and 5% hydrogen under 650 atmospheres to produce acetic acid anhydride. The acetic acid in the Reppe et al reaction mixture is used as an inert solvent for the cobalt bromide and iodide which are not well soluble in the methyl acetate, as described in Reppe et al, U.S. Pat. No. 2,789,137. The U.S. Pat. No. 2,789,137 patent additionally discloses the use of dimethyl ether as a starting material to produce acetic acid anhydride, and that the mixture of carbon monoxide and hydrogen must contain at least 60% carbon monoxide.

Paulik et al, U.S. Pat. No. 3,769,329, disclose the preparation of carboxylic acids and esters from alcohols with carbon monoxide in the presence of a rhodium and halogen catalyst to overcome the formation of undesirable by-product methane when the carbon monoxide contains an inert impurity of hydrogen. The undesirable gaseous by-product methane is disclosed to be a product of the water gas shift reaction catalyzed by cobalt.

Kuckertz, U.S. Pat. No. 4,046,807, produces acetic anhydride by reacting methyl acetate and carbon monoxide in the presence of a Group VIII metal and iodide. Hydrogen present in large quantities, 5–50% by volume, reduces soot formation and $CO_2$, and provides an increased formation of acetic acid. Methane formation is nowhere addressed.

Rizkalla, U.S. Pat. No. 4,115,444, produces a carboxylic acid anhydride from an carboxylate ester or hydrocarbyl ether by the carbonylation of the ester with carbon monoxide in the presence of a Group VIII noble metal promoted with a metal of Group IVB, VB, VIB, or VIII, and an organo-nitrogen or organo-phosphorus compound. Rizkalla discloses a solvent of a carboxylic acid can be used which, preferably, should correspond to the anhydride being produced. The carbon monoxide should be substantially pure, but hydrogen present as an impurity is not objectionable.

Rizkalla et al in German Application No. 2610035 produce ethylidene diacetate by carbonylating dimethyl ether or methyl acetate in the presence of hydrogen and additionally disclose the production of by-product acetic anhydride and acetic acid. Acetic acid can be used as solvent or diluent to facilitate the liquid phase reaction. As such, acetic acid can be present in the range of 1 to 75 mole % of the reaction medium in the liquid phase. Formation of ethylidene diacetate requires a $CO/H_2$ molar ratio of 2:1 to 4:1 depending on whether dimethyl ether or methyl acetate is used as the starting material. A broader range of $CO/H_2$ of a 1:100 to 100:1 molar ratio is disclosed, and the range of 0.5:1 to 5:1 $CO/H_2$ molar ratio is preferred. The acetic anhydride by-product depends largely on the ratio of carbon monoxide to hydrogen used. The molar ratio of by-product acetic anhydride/acetic acid can be increased by increasing the molar ratio of $CO/H_2$. Examples are given using very high $CO/H_2$ ratios in which significant quantities of acetic anhydride are produced, e.g. in amounts as high as 75% of the product with acetic acid present in the amount of 3%. An example producing 42% acetic anhydride using a 1 to 2 $CO/H_2$ ratio produces substantial quantities of acetic acid. The reference nowhere discloses the amount of methane formed in the examples.

Intille, U.S. Pat. No. 4,067,900, shows in Example 10 that the hydrogenolysis of methyl acetate with a mixture of hydrogen/carbon monoxide in a very high molar ratio forms methane product. Acetic acid is used as solvent and produced as product, but quantities are not disclosed. The catalyst included an iridium component and iodide component.

The use of a mixed hydrogen and carbon monoxide atmosphere, such as in a 1/1 molar ratio, would be desirable and economically advantageous in the carbonylation reaction of carboxylic acids to form carboxylic acid anhydrides. However, the use of such a mixed gas atmosphere leads to the production of acetic acid, acetaldehyde, ethylidene diacetate, and methane as by-product compounds. The co-production of methane is of particular concern and has presented an economic obstacle to a process for forming carboxylic acid anhydrides using such a mixed hydrogen/carbon monoxide atmosphere because of the detriment to high selectivities and the expense of purging or eliminating methane from the system by conventional methods.

SUMMARY OF THE INVENTION

In accordance with my invention, a carboxylic acid ester and a synthesis gas are reacted to produce a carboxylic acid anhydride in high yield in the presence of an iodide promoted catalyst containing a noble metal of the eighth subgroup of the periodic table and a side-reaction-inhibiting amount of carboxylic acid having an acyl group corresponding to the acyl moiety of the carboxylic acid ester. The synthesis gas mixture of hydrogen and carbon monoxide contains hydrogen at a volume percent level ranging from about 33% to about 80%. Reaction temperatures can range from about 125° C. to about 250° C., and pressures are in the range of from about 5 atmospheres to about 100 atmospheres. Although numerous Group VIII metals may serve as the catalyst, rhodium compounds are preferred and provide excellent results when promoted with an iodide. A chromium compound, e.g., chromium carbonyl or chromium (II) iodide may be used as an additional promoter to boost the inhibiting effect.

It is an object of my invention to provide a process for the production of carboxylic acid anhydride from carboxylic acid ester using a mixed synthesis gas atmosphere.

It is an object of my invention to inhibit the production of undesirable by-product methane without the need for high pressures in the process.

It is another object of my invention to provide a by-product gas mixture from the use of synthesis gas in the reaction, which by-product gas mixture is depleted in carbon monoxide and enriched in hydrogen and is thereby suitable for use in hydrogenating processes and systems or with hydrogenation catalysts.

It is a further object of my invention to provide a process which achieves high selectivity to carboxylic acid anhydride using a synthesis gas feed.

It is still further an object of my invention to provide a method of producing carboxylic acid anhydride in which the rate of carbonylation is improved over reactions run without the addition of a side-reaction-inhibiting amount of the appropriate inhibitor compound in the process of my invention.

DETAILED DESCRIPTION OF INVENTION

It has been found that carboxylic acid anhydrides are produced from carboxylic acid esters using a mixed hydrogen/carbon monoxide synthesis gas atmosphere while reducing undesirable by-products by the addition of a carboxylic acid inhibitor such that the reaction is carried out in the presence of said carboxylic acid inhibitor in side-reaction-inhibiting amounts. The carboxylic acid inhibitor is selected such that its acyl group corresponds to the acyl moiety of the carboxylic acid ester. Preferably, the carboxylic acid inhibitor contains from 2-20 carbon atoms.

The synthesis gas mixture, comprising a mixture of hydrogen and carbon monoxide, can contain hydrogen in an amount of about 33% to about 80% of the gaseous volume. A mixed hydrogen/carbon monoxide atmosphere of about 1/1 molar ratio, e.g., a gas mixture having a volume percent hydrogen in the range of from about 45% to about 55%, is preferred for the reason that such an atmosphere can be obtained economically from common synthesis gas sources.

The addition of a side-reaction-inhibiting amount of the carboxylic acid inhibitor unexpectedly blocks methane formation in the reaction. I have found that the effect of adding the inhibitor compound is not merely one of rate enhancement of the desired reaction, while leaving the absolute rate of methane formation unchanged. Rather, preferred conditions show both an acceleration in absolute rate of the desired reaction and a suppression of methane formation to abnormally low levels. Absent the addition of a side-reaction-inhibiting amount of the carboxylic acid inhibitor, significant quantities of methane are formed depending on the hydrogen partial pressure and the exact nature of the catalyst system.

The side-reaction-inhibiting compound in the process of my invention, i.e., the appropriate carboxylic acid, functions as an inhibitor rather than a mere proton donor as might be expected. The appropriate carboxylic acid inhibitor functions to inhibit certain side reactions which would otherwise produce undesirable by-products such as methane, aldehyde, and alkylidene dicarboxylate. The function of inhibiting methane from the by-product mix is particularly desirable and unexpected. Experimental data clearly show other proton donors, e.g. water, methanol, sulfuric acid, and phosphoric acid do not provide the desired results. Mineral acids or Bronsted acids as a class thereby cannot produce the results of the appropriate carboxylic acid inhibitor selected for the process of my invention.

My invention is aimed at the production of a useful mixture of carboxylic acid anhydride and a hydrogen enriched blend of CO and hydrogen under conditions which are expected by the prior art to produce alkylidene dicarboxylate. While I do not wish to be limited by the following hypothesis, I believe that the addition of the carboxylic acid inhibitor to the initial reaction mixture, or otherwise composing the reaction mixture so that the reaction is substantially carried out in the presence of the carboxylic acid inhibitor, (as contraposed to the anticipated appearance of carboxylic acid as a normal reaction product) serves to inhibit the production of methane by the following means: The normal course of the reaction to produce an alkylidene dicarboxylate, e.g., ethylidene diacetate by the carbonylation of methyl acetate ($CH_3COCH_3$) in the presence of hydrogen produces an intermediate (1) where X may be iodine or a composition of rhodium.

$$CH_3COX \qquad (1)$$

This intermediate, and not an iodide promoter, e.g., methyl iodide, directly is the source of a disadvantageous reaction with $H_2$ and production of methane. Adding acetic acid inhibitor to the initial reaction mixture causes the destructive reaction of this intermediate, thereby boosting acetic anhydride formation and decreasing methane formation. The case of added acetic acid is clearly different from the case of acetic acid produced during the course of ethylidene diacetate production, for I have determined that such conditions (1) do not lead to acetic anhydride as the principle liquid product (2) do not lead to an $H_2$ enriched synthesis gas composition and (3) do not decrease the methane produced by the system.

One reason that a carboxylic acid generated during the course of the run is not an effective inhibitor for the process of my invention is that during a reaction, CO is consumed from the headspace gas much more rapidly than is hydrogen. By the time a carboxylic acid concentration has built up sufficiently to begin to affect the reaction, the predominant reaction has become hydrogenation.

The rate expression (2), where M is the metal, e.g. rhodium, and $MH_2$ is a reactive metal hydride, helps to describe this phenomenon in the case of acetic acid.

$$-d[CH_3COX]/dt = K_1[CH_3COX][MH_2] + K_2[CH_3COOH][CH_3COX] \qquad (2)$$

As the reaction procedes normally, both $CH_3COOH$ and $MH_2$ undergo increases in concentration as the reaction depletes the original charge of carbon monoxide. Methane is of course being produced all the while that the acetic acid concentration is increasing. If acetic acid is added at the beginning of a reaction, $MH_2$ is low and the reaction is driven to acetic anhydride formation.

I have found that when $H_2$ build-up is minimized (by not running a continuous gas make-up), carboxylic acid inhibitor levels of about 7-14 wt. % are sufficient to bring about complete inhibition of the methane reaction. Naturally the minimum carboxylic acid content is desired in order to minimize separation costs of carboxylic acid and anhydride. Thus, while there is no upper limit on the effect of inhibition, there is an upper limit on an economic basis.

The side-reaction-inhibiting amount of a selected carboxylic acid inhibitor can range from about 5% to about 95% by weight of the liquid reactant mixture, i.e., initial reactants. In the case of acetic anhydride production, an amount of acetic acid in a range of about 7% to about 60% by weight of initial liquid reactants is preferable, and a range of about 10% to about 40% by weight is more preferable.

My process is catalyzed with a noble metal of the eighth subgroup of the periodic table and the salts thereof. The reaction catalyst preferably is rhodium or a rhodium compound, e.g. rhodium chloride and is preferably promoted with an iodide compound, e.g. methyl iodide. Chromium-containing and other Group VI compounds, e.g. molybdenum and tungsten, perform very favorably to promote the rate of carbonylation. Chromium carbonyl or chromium (II) species enhance the reaction rate of my process and, in the presence of an acetic acid inhibitor, anticipated products of the decomposition of chromium (O) or chromium (II) species, such as chromium (III) acetate, have no measurably adverse effect on the inhibited reaction of my invention.

The group eight metal catalyst is employed in an amount which can vary over a wide range, e.g. 1 mole per 10 to 100,000 moles of ester, preferably 1 mole per 100 to 10,000 moles of ester, and more preferably 1 mole per 300 to 2500 moles of ester. The ratio of ester to the iodide in the reaction system can vary over a wide range, e.g. typically 0.1 to 1000 moles of ester per mole of iodide, and preferably 1 to 60 moles ester to mole of iodide. The amount of metal promoter can vary widely, and typical quantities are in the range of one mole per 1 to 10,000 moles of ester, preferably 1 mole per 10 to 2000 moles, and more preferably 1 mole per 20 to 200 moles of ester.

The reaction may be carried out at temperatures ranging from 125° C. to about 250° C., and the pressure of reaction can range from about 5 atmospheres to about 100 atmospheres.

The method of my invention provides for the coproduction of a gas mixture depleted in carbon monoxide and enriched in hydrogen suitable for use with hydrogenation catalysts which tolerate or require a partial pressure of carbon monoxide.

STATEMENT OF INDUSTRIAL APPLICATION

The method of my invention provides for the production of acetic anhydride, which is used in large commercial quantities, from methyl acetate and synthesis gas at lower pressures, which without my improvement would produce significant quantities of methane by-product and present an economic obstacle to a commercial process of this type. The use of synthesis gas over essentially pure carbon monoxide and the low to moderate reaction pressures provide economic advantages. Further, the invention provides an improved reaction rate in addition to the suppression of methane formation.

The following examples describe the improvements provided by my invention. Experimental conditions highlight the nature of my invention, but are not intended to limit the scope thereof.

EXAMPLE 1

A one liter autoclave of Hastelloy-C metal fitted with a magnetic drive turbine stirring shaft and propeller was charged with 4.0 moles methyl acetate, 0.069 mole methyl iodide, 0.0019 mole $RhCl_3.3H_2O$, 0.0162 mole 3-picoline and an initial charge of carbon monoxide and hydrogen at a 1/1 mole ratio at 1500 psig, which gas charge was not replenished during the run. The autoclave was heated to reach and maintain an internal temperature of 150° C. The liquid was stirred at 1000 rpm for 15 hours, and then cooled to room temperature. The results are listed in Table 1 under Run 1.

Run 2 differed from Run 1 only in that 0.87 mol acetic acid was included in the initial charge of reaction mixture. An analysis of the head gases and liquids is presented in Table 1.

TABLE 1

| | Product Composition | |
|---|---|---|
| | Run 1 | Run 2 |
| Liquid (moles) | | |
| Acetic Acid | 0.220 | 0.86 |
| Acetic Anhydride | 0.174 | 0.292 |
| Ethylidene Diacetate | 0.126 | 0.021 |
| Gases (moles) | | |
| Methane | 0.078 | 0. |
| Hydrogen | −0.206 ($H_2$ consumed)* | −0.107 ($H_2$ consumed)* |
| Gases (volume) | | |
| Carbon Monoxide/Hydrogen | 2/3 | 2/3 |
| Methane | 0.45% | 0% |
| Final Pressure (psig) | 1060 | 1225 |

*Change in moles of hydrogen in reactor (final minus initial).

A comparison of Run 2 to Run 1 shows the elimination of methane formation as a by-product in Run 2 while increasing anhydride and decreasing ethylidene diacetate formations. Run 2 produces a hydrogen-enriched synthesis gas, but since the reaction was run with a non-replenished initial charge of gas, a net decrease of hydrogen in the vessel is observed. The decrease of hydrogen in Run 2 is less by a factor of about 2.

EXAMPLE 2

The reactor of Example 1 was charged with 5.0 moles methyl acetate, 0.69 mole methyl iodide, 0.0038 mole $RhCl_3.3H_2O$, and 0.2394 mole pyridine. The reaction was run at 150° C. and a 2/1 carbon monoxide/hydrogen mole ratio mixture was added continuously to maintain the total pressure of 1000 psig. After three hours, the reaction mixture was cooled to room temperature. The results are shown as Run 1 in Table 2.

Run 2 differed from Run 1 only in that 1.76 moles of acetic acid was added as an initial reactant.

TABLE 2

| | Product Composition | |
|---|---|---|
| | Run 1 | Run 2 |
| Liquid (moles) | | |
| Acetic Acid | 0.721 | 2.13 |
| Acetic Anhydride | 0.513 | 1.20 |
| Ethylidene Diacetate | 0.592 | 0.32 |
| Gases (moles) | | |
| Methane | 0.058 | 0.022 |
| Hydrogen | 0.2203* | 0.414* |
| Gases (volume) | | |
| Carbon Monoxide/Hydrogen | 1.02/1 | 1/2.5 |

TABLE 2-continued

| Product Composition | | |
|---|---|---|
| | Run 1 | Run 2 |
| Methane | 0.038% | 0.020% |

*Change in moles of $H_2$ in reactor (final minus initial).

The results show a clear decrease in methane formation in Run 2. Further, higher positive values of hydrogen in Run 2 indicate lower chemical consumption of hydrogen and greater efficiency in producing a hydrogen-enriched gas, since a 2/1 carbon monoxide/hydrogen mixture is continuously added to maintain pressure.

EXAMPLE 3

The experiment of Example 2 was repeated with the only difference that 0.12 mole of chromium acetate $Cr(OAc)_3$ was added to the reaction mixture in both Runs 1 and 2. An analysis of the products is presented in Table 3.

TABLE 3

| Product Composition | | |
|---|---|---|
| | Run 1 | Run 2 |
| Liquid (moles) | | |
| Acetic Acid | 0.68 | 2.20 |
| Acetic Anhydride | 0.46 | 1.48 |
| Ethylidene Diacetate | 0.07 | 0.09 |
| Gases (moles) | | |
| Methane | 0.105 | 0.018 |
| Hydrogen | 0.198* | 0.64* |
| Gases (volume) | | |
| Carbon Monoxide/Hydrogen | 1/1 | 1/6.6 |
| Methane | 0.069%* | 0.016%* |

*Change in moles of $H_2$ in reactor (final minus initial).

Run 2 clearly shows that the addition of acetic acid in the initial charge has a significant effect on reducing methane and increasing the hydrogen content of the head gas.

EXAMPLE 4

The apparatus of Example 1 was charged with 5.0 moles methyl acetate, 0.58 mole methyl iodide, 3.0 moles acetic acid, 0.013 mole $RhCl_3 \cdot 3H_2O$, 0.045 mole $Cr(CO)_6$, and 0.099 mole triphenyl phosphine, and pressurized to 1000 psig with a gas mixture of 2 parts carbon monoxide and 1 part hydrogen by volume. The reaction mixture was heated and maintained at 175° C. The reactor pressure was maintained at 1000 psig by the regulated addition of the 2/1 $CO/H_2$ gas mixture. An analysis of the liquid phase after one-half hour showed 3.1 moles methyl acetate, 3.2 moles acetic acid, 1.5 moles acetic anhydride, and 0.12 mole ethylidene diacetate. The composition of the gas phase of the product was estimated to be enriched to 80% hydrogen. Methane was less than 0.06 mole.

The data show that reaction selectivity is general as to ligands, and to high concentrations of acetic acid.

EXAMPLE 5

The reaction rates and relative selectivities for each run in Examples 1–4 were determined and are shown in Table 4.

A high selectivity to form the acetic anhydride is clearly shown in the Product Mole Ratios data from those runs which carried out the reaction in the presence of inhibitor according to the process of my invention.

Higher conversion rates are observed in those runs practicing my process by carrying out the reaction in the presence of inhibitor and further providing a continuous addition of the $H_2/CO$ gas mixture to maintain pressure.

TABLE 4

| | Example 1 | | Example 2 | | Example 3 | | Example 4 |
|---|---|---|---|---|---|---|---|
| | Run 1 | Run 2 | Run 1 | Run 2 | Run 1 | Run 2 | |
| Rate (moles $Ac_2O$/mole Rh hr.)[2] | 6 | 10 | 135 | 315 | 121 | 390 | 230 |
| % Conversion[2] | 13 | 8 | 37 | 38 | 24 | 40 | 36 |
| Product Mole Ratios | | | | | | | |
| $Ac_2O/AcOH$[3] | 0.79 | 2.95 | 0.7 | 3.24 | 0.68 | 3.36 | 7.5 |
| $Ac_2O/EDA$[4] | 1.38 | 13.9 | 0.87 | 3.8 | 6.6 | 16.4 | 12.5 |
| $Ac_2O/CH_4$[5] | 2.23 | .292/0[6] | 9 | 55 | 4.4 | 82 | 25 |
| $H_2$ in reactor (moles) | −0.21 | −0.11 | 0.2 | 0.41 | 0.198 | 0.41 | 0.516 |

[1] $Ac_2O$ = acetic anhydride, Rh = Rhodium

[2] % Conversion = $\left[ 1 - \frac{(MeOAc_{(i)} - (AcOH - AcOH_o - EDA) - Ac_2O - 2EDA)}{MeOAc_i} \right] \times 100$ where MeOAc(i) = initial methyl acetate and $AcOH_o$ = Initial acetic acid added, if any
[3] AcOH = acetic acid
[4] EDA = ethylidene diacetate
[5] $CH_4$ = methane
[6] Infinity, i.e. with respect to the limits of this analysis

EXAMPLE 6

The experimental of Example 4 was run with the difference of replacing acetic acid by an equal molar amount of sulfuric acid, phosphoric acid, water, or methanol. The products are shown in Table 5.

TABLE 5

| Effect of Bronsted Acids on $Ac_2O$ Production | | | | | |
|---|---|---|---|---|---|
| Product | | $H_2O$ | MeOH | $H_2SO_4$ | $H_3PO_4$ |
| MeOAc | (moles) | 1.56 | 6.3 | 3.85 | 2.32 |
| HOAc | (moles) | 5.17 | 0.02 | 1.44 | 3.32 |
| $Ac_2O$ | (moles) | 0 | 0 | 0 | 0 |
| EDA | (moles) | 0 | 0 | 0 | 0 |
| $CH_4$ | (moles) | 0.104 | 0.023 | 0 | 0.01 |

MeOAc = methyl acetate, HOAc = acetic acid, $Ac_2O$ = acetic anhydride, EDA = ethylidene diacetate, and $CH_4$ = methane Example 6 shows the lack of utility of mineral acids or Bronsted acids as a class. When a mere proton donor was substituted for acetic acid in equal molar proportions, the substituted proton donor failed to effect any acetic anhydride formation.

What is claimed is:

1. A process for the production of carboxylic acid anhydride from carboxylic acid ester and synthesis gas comprising reacting a feed gas mixture of hydrogen and carbon monoxide in which the volume percent hydrogen ranges from about 33% to about 80% with a liquid reactant mixture comprising carboxylic acid ester at a temperature in the range of from about 125° C. to about 250° C. and a pressure in the range of from about 5 atmospheres to about 100 atmospheres in the presence of an iodide promoted catalyst containing a noble metal of the eighth subgroup of the periodic table and a side-reaction-inhibiting amount of a carboxylic acid inhibitor having an acyl moiety corresponding to the acyl moiety of said carboxylic acid ester.

2. The process of claim 1 wherein said carboxylic acid inhibitor has an acyl moiety having 2–20 carbon atoms.

3. The process of claim 2 wherein a by-product gas mixture enriched in hydrogen is produced.

4. The process of claim 3 wherein said carboxylic acid inhibitor is present in the range of from 5% to about 95% by weight of said liquid reactant mixture.

5. The process of claim 4 wherein said catalyst contains a chromium compound.

6. The process of claim 5 wherein said catalyst is promoted with methyl iodide.

7. The process of claim 6 wherein said carboxylic acid anhydride is acetic anhydride, said carboxylic acid ester is methyl acetate, and said carboxylic acid inhibitor is acetic acid.

8. The process of claim 7 wherein said acetic acid is present in the range of from 7% to about 60% of said liquid reactant mixture.

9. The process of claim 8 wherein said acetic acid is present in the range of from about 10% to about 40% of the liquid reactant mixture.

10. The process of claim 9 wherein said feed gas mixture has a volume percent hydrogen in the range from about 45% to about 55%.

* * * * *